(12) United States Patent
Deprez et al.

(10) Patent No.: US 11,573,500 B2
(45) Date of Patent: Feb. 7, 2023

(54) METAL COMPOUND, USE OF THE METAL COMPOUND AS A CHARGE CONTROL AGENT COMPOSITION AND A CHARGEABLE TONER COMPOSITION

(71) Applicant: XEIKON MANUFACTURING N.V., Lier (BE)

(72) Inventors: Lode Erik Dries Deprez, Lier (BE); Karlien Maria Hugo Renata Torfs, Boechout (BE); Geert Gaston Paul Deroover, Lier (BE)

(73) Assignee: XEIKON MANUFACTURING N.V., Lier (BE)

( * ) Notice: Subject to any disclaimer, the term of this patent is extended or adjusted under 35 U.S.C. 154(b) by 0 days.

(21) Appl. No.: 16/977,121

(22) PCT Filed: Mar. 13, 2019

(86) PCT No.: PCT/EP2019/056223
§ 371 (c)(1),
(2) Date: Sep. 1, 2020

(87) PCT Pub. No.: WO2019/175208
PCT Pub. Date: Sep. 19, 2020

(65) Prior Publication Data
US 2021/0003935 A1 Jan. 7, 2021

(30) Foreign Application Priority Data
Mar. 13, 2018 (NL) .................................. 2020578

(51) Int. Cl.
*C07C 217/28* (2006.01)
*C07F 3/06* (2006.01)
(Continued)

(52) U.S. Cl.
CPC ....... *G03G 9/09791* (2013.01); *C07C 217/28* (2013.01); *C07F 3/06* (2013.01); *G03G 9/08795* (2013.01); *G03G 15/08* (2013.01)

(58) Field of Classification Search
CPC ........... G03G 9/09791; G03G 9/08795; G03G 15/08; C07C 217/28; C07F 3/06
See application file for complete search history.

(56) References Cited

U.S. PATENT DOCUMENTS 4,404,271 A * 9/1983 Kawagishi ......... G03G 9/09783
987/5
4,771,034 A * 9/1988 Ikeda ..................... B41M 5/155
503/212

(Continued)

FOREIGN PATENT DOCUMENTS

| DE | 3144017 A1 | 7/1982 |
|----|------------|--------|
| EP | 0219302 A2 | 4/1987 |
| EP | 0762222 A2 | 3/1997 |

OTHER PUBLICATIONS

Database CA [online] Chemical Abstracts Service, Columbus, Ohio, US; 1987, XP002791237.

(Continued)

*Primary Examiner* — Peter L Vajda
*Assistant Examiner* — Jayson D Cosgrove
(74) *Attorney, Agent, or Firm* — KDB Firm PLLC

(57) ABSTRACT

A metal compound includes a metal and at least two aromatic hydroxycarboxylic acid structures. Each aromatic hydroxycarboxylic acid structure includes an aromatic moiety having a hydroxyl substituent and a carboxylic acid substituent, which cooperatively bond the aromatic moiety to the metal via at least one of ionic bond, covalent bond and coordinate bond. Each aromatic hydroxycarboxylic acid structure is bonded to a polymer segment.

18 Claims, 3 Drawing Sheets

(51) Int. Cl.
*G03G 15/08* (2006.01)
*G03G 9/087* (2006.01)
*G03G 9/097* (2006.01)

(56) References Cited

U.S. PATENT DOCUMENTS

| | | | |
|---|---|---|---|
| 9,223,240 B2 * | 12/2015 | Kenmoku | G03G 9/08708 |
| 9,280,077 B2 * | 3/2016 | Tsunemi | G03G 9/1138 |
| 2009/0202927 A1 * | 8/2009 | Yano | C08G 63/6882 |
| | | | 430/48 |
| 2012/0172562 A1 * | 7/2012 | Kenmoku | G03G 9/08706 |
| | | | 526/287 |
| 2014/0072908 A1 * | 3/2014 | Masumoto | G03G 9/09733 |
| | | | 430/108.4 |
| 2014/0080989 A1 * | 3/2014 | Yasumatsu | C08F 12/22 |
| | | | 526/292.9 |
| 2016/0139524 A1 * | 5/2016 | Okita | G03G 9/09371 |
| | | | 430/109.4 |

OTHER PUBLICATIONS

International Search Report and Written Opinion for Application No. PCT/EP2019/056223, dated May 28, 2019, 10 pages.

* cited by examiner

METAL COMPOUND, USE OF THE METAL COMPOUND AS A CHARGE CONTROL AGENT COMPOSITION AND A CHARGEABLE TONER COMPOSITION

This is a national stage application filed under 35 U.S.C. § 371 of pending international application PCT/EP2019/056223, filed Mar. 13, 2019, which claims priority to Netherlands Patent Application No. NL 2020578, filed Mar. 13, 2018, the entirety of which applications are hereby incorporated by reference herein.

FIELD OF INVENTION

The field of the invention relates to a metal compound and use of the metal compound as a charge control agent composition. The invention further relates to a chargeable toner composition comprising the metal compound according to the present invention. The invention further relates to a use of a chargeable toner composition according to the present invention for electrostatic printing.

BACKGROUND

A charge control agent composition is known to be used to provide a positive or a negative charge to a toner composition for developing electrostatic images in electrophotography, electrostatic recording, electrostatic printing, etc.

Electrostatic latent images can be developed into visible images with a toner which is caused to adhere to the image by electrostatic attraction. Besides liquid developers, powder or dry developers are widely used for developing electrostatic latent images. Static charged powder particles are also used in the field of powder coatings.

The powder developers are divided generally into two types: two-component developers comprising a toner and a carrier of iron or ferrite mixed with the toner, the toner being composed of a natural resin or synthetic resin including a coloring agent and a charge control agent, which are dispersed in the resin, and a fluidizing agent; and one-component developers comprising a natural resin or synthetic resin, including a coloring agent, a charge control agent and a magnetic material, which are dispersed in the resin, and a fluidizing agent.

With the two-component developer, the toner is triboelectrically charged by the carrier and deposited on electrostatic images for development. The one-component developers heretofore known include toners which are chargeable by friction with a brush- or blade/plate-like friction member serving the function of the carrier as a substitute therefor. Charge injection can also be a suitable process. In order to hold the toner charged, it has been proposed to impart the desired triboelectric chargeability to the toner, charge control agents are admixed with toners. Negatively charged toner compositions presently used in the art include charge control agents based on a metal complex compound of an aromatic hydroxycarboxylic acid, such as a zinc-, chromium- or zirconiumcomplex compound of a salicylic acid or a hydroxy-naphtoic acid. Herein, the aromatic hydroxycarboxylic acid is an example of a metal chelating agent.

However, it has been found that these metal complexes can decompose and create a deposition of residues of the metal compound, which is used as charge control agent composition, may occur inside the electrostatic printing device when thermally treating a toner composition for developing and/or fusing images over a longer period, the toner composition having a charge control agent, such as a zinc complex compound of a salicylic acid or a hydroxynaphtoic acid. These depositions may inhibit or disturb a proper toner developing process in the electrostatic printing device and also may give problems when these fragments start to migrate through the substrate or start to create setoff towards another, in particular above arranged, substrate in a stack of substrates whereby specific migration limits can be exceeded.

SUMMARY

Exemplary embodiments of the invention aim to provide a metal compound of a new chemical structure having excellent charge control or charge-enhancing properties and reduces a deposition of residues of the metal compound in an electrostatic printing device.

Exemplary embodiments aim to provide a metal compound being usable as a charge control agent composition for controlling a chargeability of a powder composition.

Exemplary embodiments of the invention aim to provide a chargeable toner composition comprising the metal compound having excellent charge control or charge-enhancing properties and reducing a deposition and migration of residues of the metal compound or of a metal chelating agent in an electrostatic printing device.

According to a first aspect, the invention relates to a metal compound comprising a metal and at least two aromatic hydroxycarboxylic acid structures, each aromatic hydroxycarboxylic acid structure having an aromatic moiety having a hydroxyl substituent and a carboxylic acid substituent, which cooperatively bond the aromatic moiety to the metal via at least one of ionic bond, covalent bond and coordinate bond, wherein each aromatic hydroxycarboxylic acid structure is bonded to a polymer segment.

According to a second aspect, the invention relates to a use of the metal compound according to the present invention as a charge control agent composition for controlling a chargeability of a powder composition.

According to a third aspect, the invention relates to a chargeable toner composition comprising the metal compound according to the present invention, wherein the toner composition further comprises a binder resin.

According to a further aspect, the invention relates to a use of a chargeable toner composition according to the present invention for electrostatic printing especially for an acid containing resin toner system. In this application, an acid containing resin toner system is defined as a resin having an acid value of at least 2 mg KOH/g.

It has been found, that during use of the metal compound as a charge control agent in a toner composition the metal compound may degrade, such as partly decompose in response to a thermal treatment of the toner composition, wherein the bond between the aromatic hydroxycarboxylic acid structure and the metal atom may be broken, thereby forming an aromatic hydroxycarboxylic acid structure residue. Said aromatic hydroxycarboxylic acid structure residue may easily migrate, sublimate or evaporate inside the electrostatic printing device. The ease of decomposition or degradation of the metal compound may also be dependent on the toner composition, such as predominantly depending on the choice of the binder resin. The ability of a polyesters resin to stabilize or interact with the metal complex after decomposition of the metal compound may cause that toners based on a polyesters resin are more prone to decomposition of the metal complex due to the presence of the acid functionality of the binder resin. Other resins like styrene acrylics or polyethers may perform better in respect of less decomposition of the metal complex, but have other important drawbacks, such as reduced adhesion, reduced chargeability, reduced dispersibilty of the toner ingredients like pigments, charge control agents, etc. Therefore, a polyesters resin is a preferred resin for toners, especially in colored toners, for high speed high performing digital production engines.

As the aromatic moiety of the metal compound is additionally bonded to the polymer segment, the migration and/or evaporation and/or sublimation of the aromatic hydroxycarboxylic acid structure residue is inhibited or at least drastically reduced.

In fact, the polymer segment may be selected in order to act as a ballast group of the aromatic hydroxycarboxylic acid structure residue, which at least retards a migration process of the aromatic hydroxycarboxylic acid structure residue.

As such, a new metal compound is provided which may provide that a deposition of the aromatic hydroxycarboxylic acid structure residue in an electrostatic printing device is inhibited or reduced, while maintaining a suitable charging behavior of the charge control agent composition.

A polymer segment in the context of the present invention is defined as a large molecule, or macromolecule, composed of many repeated subunits. In particular, a polymer may be characterized by the sequence of one or more types of monomer repeating units which are covalently bonded to at least one other monomer repeating unit. Thus, a polymer segment has a sequence comprising two or more repeating units, preferably three or more repeating units. In the context of this definition a repeating unit means the reacted form of a monomer in the polymer. The polymer segment has a polydispersity D, which is a measure of the heterogeneity of molecular weight of the polymer segments over the molecules of the metal compound. The polydispersity can be calculated using the equation $D=M_w/M_n$, where Mw is the weight-average molar mass and Mn is the number-average molar mass of the polymer segment. The polydispersity D of the polymer segment may be in the range of 1.0-3.0, preferably in the range of 1.05-2.00.

In particular embodiments, a first polymer segment of a first aromatic hydroxycarboxylic acid structure and a second polymer segment of a second aromatic hydroxycarboxylic acid structure are equal to one another or are different with respect to one another.

The polymer segment may in embodiments have a certain weight or chain length, which is substantially identical for each polymer segment of the charge control agent composition, and may have a certain weight or chain length, which is distributed over a range of weights or chain lengths wherein differences in the weights or chain lengths are primarily attributable to differences in the number of repeating units. Preferably, the total weight of the metal compound as a whole is above 1000 Dalton, more preferably the weight of the individual aromatic hydroxycarboxylic acid structure is above 1000 Dalton.

In particular embodiments, the polymer segment is bonded to at least two aromatic hydroxycarboxylic acid structures, thereby connecting a first aromatic hydroxycarboxylic acid structure to a second aromatic hydroxycarboxylic acid structure. The polymer segment of this embodiment is a bridging polymer segment, which is bonded to both aromatic hydroxycarboxylic acid structures, thereby forming a structural link or bridge between both aromatic hydroxycarboxylic acid structures. Said structural link or bridge has the advantage that both aromatic hydroxycarboxylic acid structures need to be released from the metal atom before a loose aromatic hydroxycarboxylic acid structure residue is formed. In case only one aromatic hydroxycarboxylic acid structure is released from the metal atom, it remains connected to the metal atom via the other hydroxycarboxylic acid structure and the polymer segment, which forms a structural link to the other hydroxycarboxylic acid structure.

In a typical example of the aromatic hydroxycarboxylic acid structure residue, none of the hydroxyl substituent and carboxylic acid substituent of the residue of the aromatic hydroxycarboxylic acid structure is bonded anymore to the metal.

In further embodiments of the invention, the aromatic hydroxycarboxylic acid structure residue may be further decomposed under certain conditions. For example, by way of a decarboxylation reaction scheme a second residue may be formed from the aromatic hydroxycarboxylic acid structure residue, thereby forming a hydroxyl substituted aromatic structure. For example, in case of a tert-butylsalicylic acid residue, a tert-butylphenol residue may be formed therefrom due to a decarboxylation reaction. This second residue may also present a problem of migration, sublimation, smell and deposition in the electrostatic printing device. The polymer segment may inhibit or mitigate a migration and deposition of this second residue, due to its ballast function.

In an exemplary embodiment, the weight average molecular weight Mw of the aromatic hydroxycarboxylic acid structure including the polymer segment is at least 500 g/mol, preferably is at least 1000 g/mol.

In particular exemplary embodiments, the weight average molecular weight Mw of the aromatic hydroxycarboxylic acid structure including the polymer segment is in the range of 500 g/mol-5000 g/mol, preferably in the range of 1000 g/mol-2500 g/mol.

In particular exemplary embodiments, the weight average molecular weight Mw of the aromatic hydroxycarboxylic acid structure including the polymer segment is at most 5000 g/mol, preferably at most 3500 g/mol, more preferably at most 2500 g/mol.

In an exemplary embodiment, the metal is selected from a zirconium atom, a calcium atom, an aluminum atom, a chromium atom, an iron, a boron atom and a zinc atom, preferably the metal being a zinc atom. A metal of the metal compound according to the present invention is a metal atom. Each of these metal atoms may suitably form a metal compound according to the present invention together with the at least two aromatic hydroxycarboxylic acid structures, each aromatic hydroxycarboxylic acid structure having an aromatic moiety having a hydroxyl substituent and a carboxylic acid substituent.

In an exemplary embodiment, the aromatic moiety is selected from a group consisting of a salicylic acid, a salicylic acid having one or more additional substituents, a hydroxynaphtoic acid and a hydroxynaphtoic acid having one or more additional substituents. The additional substituents, in addition to the hydroxyl substituent and carboxylic acid substituent, are substituents of the aromatic moiety of the salicylic acid and the hydroxynaphtoic acid, respectively. In case of the salicylic acid, the aromatic moiety comprises a phenyl ring structure. In case of the hydroxynaphtoic acid, the aromatic moiety comprises a naphtyl ring structure. The additional substituents may comprise one or more alkyl groups, such as a $C_4$-$C_9$ alkyl group, in particular a tert-butylgroup, may comprise one ore more hydroxyl groups, may comprise one or more halogen groups, may comprise one or more sulphonic acid groups, may comprise one or more amine groups, may comprise one ore more amide groups and may comprise one or more ester groups.

In an exemplary embodiment, the polymer segment comprises at least one of an alkyleneoxide group, an olefin group, an ester group, an acrylic group, a vinylether group, a vinylester group, and a vinylamide group.

Preferably, the polymer segment is a copolymer comprising at least one of an ethylene oxide repeating unit, a propylene oxide repeating unit and a butylene oxide repeating unit, preferably comprising a poly(ethylene oxide) group and a poly(propylene oxide) group.

Alternatively or additionally, the polymer segment may comprise a polyacrylic group and/or a polymethacrylic group and/or a polyurethane group.

Alternatively or additionally, the polymer segment may comprise a polyolefin polymer, which is modified by an amine group. Said amine modified polyolefin polymer may be a polyethylene polymer or a propylene polymer, which is amine modified. Such an amine modified polyolefin polymer is also known as a long-chain alkylpolyamine. A long-chain alkylpolyamine is preferably used for a positively charging system.

Alternatively or additionally, the polymer segment may comprise a polyethylene polymer or a propylene polymer, which is acid modified or alcohol modified, such as Unilin™, Unicid™ and Ceramer™ products obtainable from Baker Hughes.

In an exemplary embodiment, the weight average molecular weight Mw of the polymer segment is at least 500 g/mol. The higher molecular weight enhances the ballast function of the polymer segment.

In particular exemplary embodiments, the weight average molecular weight Mw of the polymer segment is in the range of 500 g/mol-5000 g/mol, preferably in the range of 1000 g/mol-2500 g/mol.

In an exemplary embodiment, each aromatic hydroxycarboxylic acid structure further comprises a bonding group configured for bonding the polymer segment to the respective aromatic moiety. In an exemplary embodiment, the bonding group is selected to bond the polymer segment to the aromatic moiety in such a way, that a charging control behavior of the metal compound as a charge control agent composition of the toner composition is substantially not effected.

In exemplary embodiments, the bonding group is a substituent of the aromatic moiety and is configured for forming an ionic bond to the polymer segment.

In alternative embodiments, the polymer segment is covalently bonded to the aromatic moiety. In particular examples, the bonding group comprises at least one of an amide, such as a monoamide or a diamide, and a carboxylic acid ester.

According to the third aspect, the invention relates to a chargeable toner composition comprising the metal compound according to the present invention, wherein the toner composition further comprises a binder resin.

Positive and negative charge control agents can be used to adjust the triboelectric chargeability of a chargeable toner composition in either negative or positive direction.

In particular, a charge control agent based on a metal compound according to the present invention is particular advantageous as it may be substantially colourless. In fact, prior art charge control agents based on a metal complexes of salicylate, such as Bontron E84 and Bontron E88, are found to be suitable for colour applications because they are colourless.

In exemplary embodiments, the binder resin is selected from at least one of a styrene resin, a styrene-acrylic resin, a styrene-butadiene resin, an epoxy resin, a polyester resin and a paraffin wax. In a preferred embodiment, the binder resin is a polyester resin.

In particular embodiments, the metal compound may be dispersed in a toner having at least one binder resin.

The polymer segment of the metal compound, which is bonded to the aromatic moiety, preferably is selected such that it has a certain chemical compatibility with the at least one binder resin of the toner such that the metal compound can be substantially evenly distributed inside the at least one binder resin of the toner. This polymer segment may or may not reduce the Tg of the at least one binder resin in a significant way.

In exemplary embodiments, at least a part of the metal compound is present at an outer surface of toner particles of the chargeable toner composition.

In an exemplary embodiment, the metal compound is preferentially arranged at an outer surface of toner particles of the chargeable toner composition. A typical example of a method for preparing chargeable toner compositions having a charge control agent, which is deposited at an outer surface of toner particles, can be found in EP01930780, in particular see paragraph [0103], which is hereby incorporated by reference. Said method described in EP01930780 may be used to preferentially deposit the metal compound according to the present invention at an outer surface of toner particles.

Toner particles according to the present invention can be prepared by any method known in the art. Those toner particles can be prepared by melt kneading the toner ingredients (e.g. toner binder resin(s), charge control agent(s), pigment(s), etc). After the melt kneading the mixture is cooled and the solidified mass is pulverized and milled and the resulting particles classified. After the classifying step an optional rounding step may be performed followed by the mounting of optional surface additives.

Toner particles useful in this invention can have an average volume diameter (size) between about 3 and 20 μm. When the toner particles are intended for use in colour imaging, it is preferred that the volume average diameter is between 4 and 12 μm, most preferred between 5 and 10 μm. The particle size distribution of said toner particles can be of any type. It is however preferred to have an essentially (some negative or positive skewness can be tolerated, although a positive skewness, giving less smaller particles than an unskewed distribution, is preferred) Gaussian or normal particle size distribution, either by number or volume, with a coefficient of variability (standard deviation divided by the average) (v) smaller than 0.5, more preferably of 0.3.

Toner particles, useful in this invention, can comprise any normal toner ingredient e.g. colouring agents e.g. pigments or dyes both coloured and black, inorganic fillers, anti-slip agents, flowing agents, waxes, etc.

Toners for the production of colour images may contain organic dyes/pigments of for example the group of phtalocyanine dyes, quinacidrone dyes, triaryl methane dyes, sulphur dyes, acridine dyes, azo dyes and fluorescein dyes. Also $TiO_2$ or $BaSO_4$ can be used as a pigment to produce white toners. In order to obtain toner particles with sufficient optical density in the spectral absorption region of the colorant, the colorant is preferably present therein in an amount of at least 1% by weight with respect to the total toner composition. To improve the distribution of the colorant in the toner resin, it may be beneficial to add a so called master batch of the colorant during the toner preparation in stead of adding the pure colorant. The master batch of the colorant is prepared by dispersing a relatively high concentration of the colorant, present as pure pigment or as press cake, preferably ranging from 20 to 50% by weight in a resin, e.g. a polyester. The same master batch techniques can also be used for dispersing charge control agents and photo initiators.

In an exemplary embodiment, the chargeable toner composition is negatively chargeable. Typically, metal complexes of one or more salicylates can be used as negative charge control agents.

In exemplary embodiments, the content of the metal compound is from 0.1 to 10 parts by mass per 100 parts by mass of the binder resin. In embodiments, a content of the metal compound may be suitably selected depending on its use as either an external surface additive, which is deposited on an outer surface of toner particles, or its use as an internal additive, which is dispersed inside the binder resin or binder resins of the chargeable toner composition.

In exemplary embodiments, the binder resin has an acid value of at least 3 mgKOH/g, preferably at least 5 mgKOH/g. Especially, in case the binder resin has an acid value of at least 3 mgKOH/g, the metal compound of the present invention improves the chemical stability of the metal compound as part of the chargeable toner composition.

DETAILED DESCRIPTION OF THE INVENTION

The accompanying drawings are used to illustrate presently preferred non-limiting exemplary embodiments of devices of the present invention. The above and other advantages of the features and objects of the invention will become more apparent and the invention will be better understood from the following detailed description when read in conjunction with the accompanying drawings, in which.

DESCRIPTION OF A PRIOR ART EXAMPLE

Figure 1:
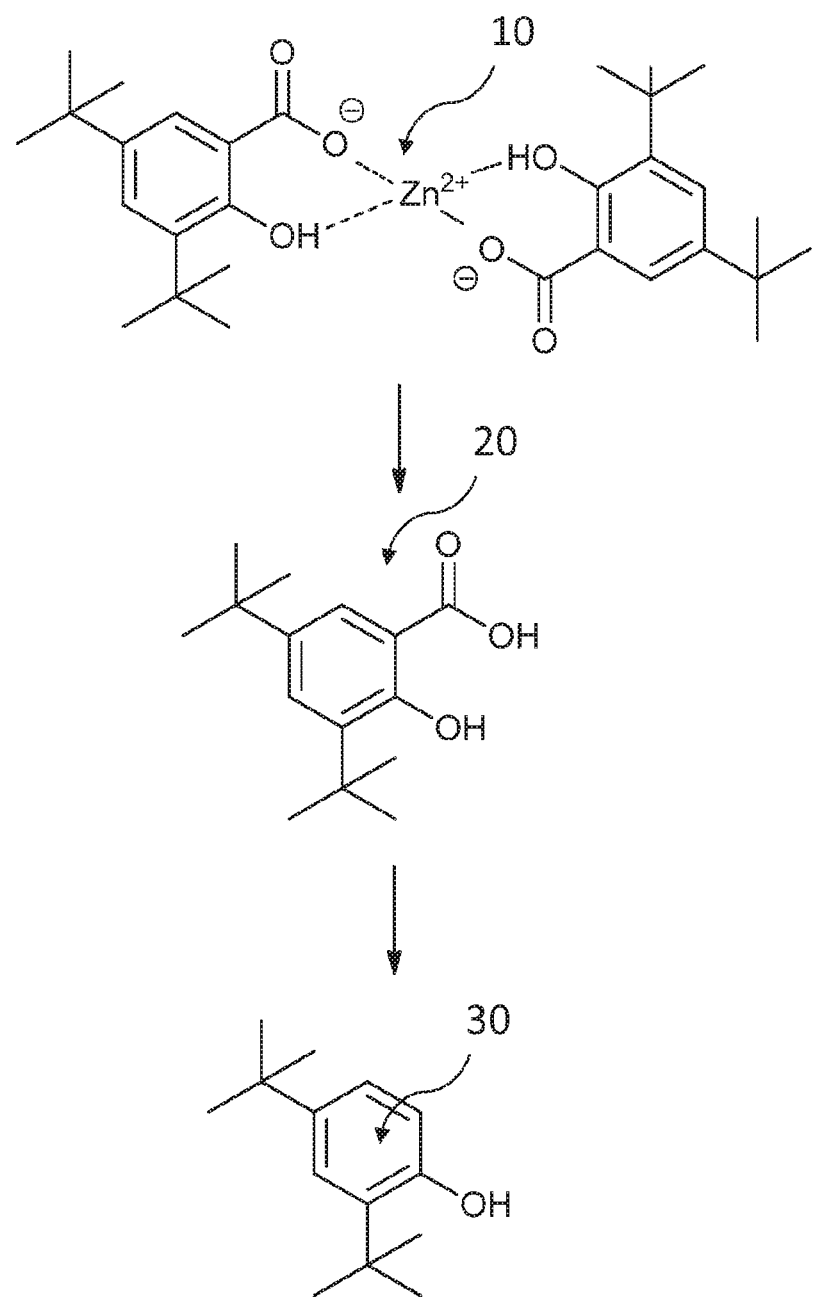
FIG. 1 illustrates schematically a decomposition flow of a metal complex of a di-tert-butylsalicylic acid.

FIG. 1 illustrates schematically a decomposition flow of a metal complex of a di-tert-butylsalicylic acid 10. As an example, the metal complex shown has a Zinc atom (Zn), which is bonded to two di-tert-butylsalicylic acid structures, wherein each di-tert-butylsalicylic acid is bonded to the zinc atom via a coordinate bonding of the hydroxyl substituent to the zinc atom and a coordinate bonding of the carboxylic acid substituent to the zinc atom.

Under certain conditions, such as during a raised temperature and/or at hygroscopic conditions and/or in the presence of an acidic group from the binder resin or other compound, the bond between the carboxylic acid substituent and the zinc atom may be broken. The hydroxyl metal bound is not that strong and this bond is not capable of keeping the complex together. As a result, a di-tert-butylsalicylic acid residue 20 is set free. This di-tert-butylsalicylic acid residue 20 is found to migrate and may also be capable to decarboxylate with the formation of a phenolic compound 30. This can happen by elevated temperature during extrusion processing of the metal complex in a toner recipe or even during fusing conditions of the toner used in an electrostatic printing device.

DESCRIPTION OF THE EMBODIMENTS

Figure 2A:
FIG. 2A-2C illustrate schematically molecular structures of a metal compound according to exemplary embodiments of the present invention.

FIG. 2A illustrates schematically a molecular structure of a metal compound according to the present invention.

In the molecular structure shown in FIG. 2A the metal compound 100 is shown wherein M represents a metal atom. The metal atom can be any metal, such as any one of suitable metals for forming a charge control agent, such as a zirconium atom, a calcium atom, an aluminum atom, a chromium atom, an iron, a boron atom and a zinc atom. Preferably, the metal atom is a zinc atom.

Figure 2B:
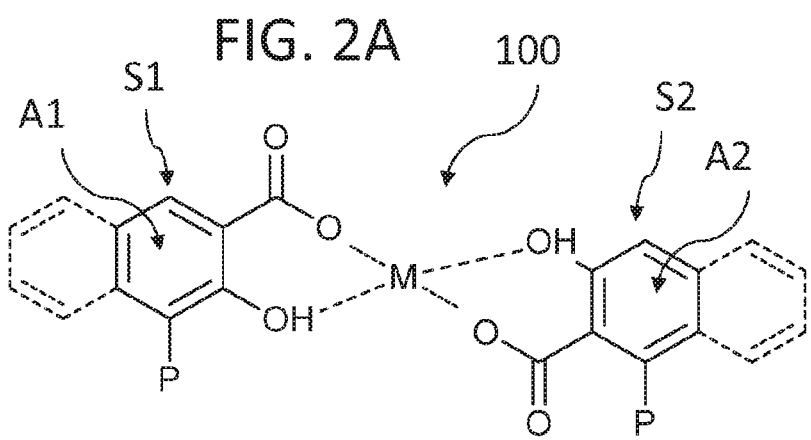

Furthermore, the metal compound 100 comprises at least two aromatic hydroxycarboxylic acid structures S1, S2. In a preferred embodiment, as shown in FIG. 2B, the metal compound 100 has two aromatic hydroxycarboxylic acid structures S1, S2. In alternative exemplary embodiments, the metal compound 100 comprises at least three aromatic hydroxycarboxylic acid structures, each aromatic hydroxycarboxylic acid structure being bonded to the metal M individually via at least one of ionic bond, covalent bond and coordinate bond.

As shown in FIG. 2B, each aromatic hydroxycarboxylic acid structure S1, S2 has an aromatic moiety A1, A2 bonded to the metal M via at least one of ionic bond, covalent bond and coordinate bond. Each aromatic moiety A1, A2 comprises an hydroxyl substituent and a carboxylic acid substituent, wherein the aromatic moiety A1, A2 is bonded to the metal M via an ionic or coordinate bond formed by at least one of the hydroxyl substituent and the carboxylic acid substituent of the aromatic hydroxycarboxylic acid part. Each of the hydroxyl substituent and the carboxylic acid substituent may be in a neutral state or may comprise an O-anion depending on the conditions of the metal compound.

Each aromatic hydroxycarboxylic acid structure S1, S2 is further bonded to a polymer segment P. In fact the polymer segment P is bonded to the respective aromatic moiety A1, A2. The polymer segment P may be bonded to the aromatic moiety in any of the substituent positions of the aromatic moiety A1, A2.

In exemplary embodiments, the aromatic ring of the aromatic moiety A1, A2 may be a phenyl ring having six substituent positions and may be a naphtyl ring structure having eight substituent positions (as is shown using intermittent lines).

In case of a naphtyl ring structure, the polymer segment P is bonded to at least one of the aromatic rings of the naphtyl ring structure.

Furthermore, the metal compound 100 may have a charge, preferably a negative charge, wherein a counter ion may be present, such as a positive counter ion. The counter ion can be changed by changing conditions, such as by changing pH conditions.

In exemplary embodiments, the polymer segment P may be bonded directly to an aromatic ring of the aromatic moiety A1, A2. In an alternative embodiments, the polymer segment P may be bonded to substituents of the aromatic hydroxycarboxylic acid part A1, A2 by way of a bonding group B.

In that case, the polymer segment P is bonded to the corresponding aromatic moiety A1, A2 via at least one bonding group B. In exemplary embodiments, the polymer segment P may be bonded to the corresponding aromatic moiety A1, A2 at two or more substituent positions of the aromatic moiety A1, A2, optionally using two or more bonding groups B, respectively.

Figure 2C:
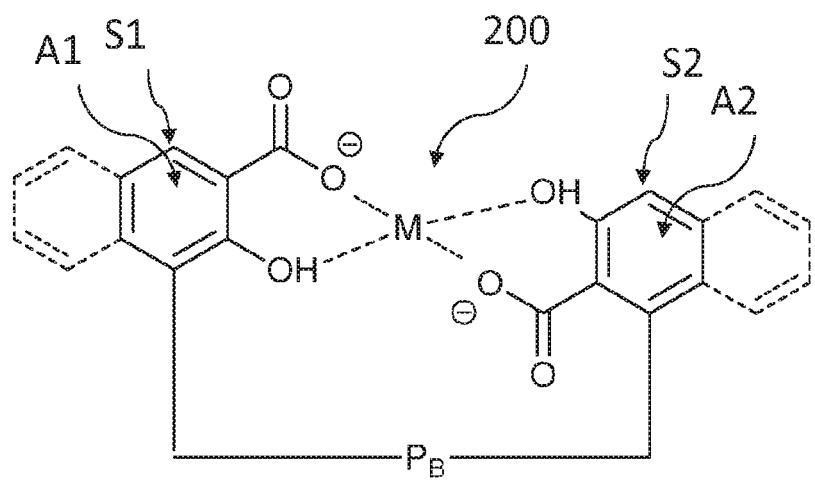

In other exemplary embodiments, as schematically shown in FIG. 2C, the polymer segment P of the metal compound 200 may be a bridging polymer segment $P_B$, which is bonded to both aromatic hydroxycarboxylic acid structures S1, S2, thereby forming a structural link or bridge between both aromatic hydroxycarboxylic acid structures S1, S2.

Optionally, additionally at least two bonding groups B may be included, wherein a first bonding group B connects the polymer segment $P_B$ to a first one of the two aromatic hydroxycarboxylic acid structures S1, and a second bonding group B connects the polymer segment $P_B$ to a second one of the two aromatic hydroxycarboxylic acid structures S2. In these examples, the polymer segment $P_B$ is a jointly polymer segment of both aromatic hydroxycarboxylic acid structures S1, S2, which forms a structural link or bridge between both aromatic hydroxycarboxylic acid structures S1, S2.

EXAMPLES

Test Methods

In order to test the metal compound, tests have been developed that are representative of the behavior of the metal compound during use. The engine deposition test is deemed representative of the depositing behavior of the aromatic hydroxycarboxylic acid structure residue of the metal compound during use in an electrostatic printing engine of a toner composition containing the metal compound. The chargeability-developability test is deemed representative for the chargeability and developability of a toner composition comprising a metal compound.

Deposition of Aromatic Hydroxycarboxylic Acid Structure Residue

Engine Test 50.000 substrates were printed with a Xeikon 9600 print engine at a speed of 16 cm/s and a substrate temperature close to the IR fuser of 125° C. on a Digilaser color 100 gsm paper substrate obtained from UPM and providing a toner-flow of 300 mg/s in total (i.e. being the sum of all toners applied). After that, a visual observation of deposition of aromatic hydroxycarboxylic acid structure residue was performed just above the IR fuser. A ranking of the amount of deposition of aromatic hydroxycarboxylic acid structure residue is as follows 1: OK-almost no "white" deposition was observed
2: acceptable-some white deposition visible
3: NOK: clearly white deposition visible Thermal Desorption Thermal desorption of a printed tonersample is performed at 130° C. during 10 min with online cryofocus on Tenax TA at 100° C. The trapped components are injected with flash heating at 290° C. and analysed by GCMS. A qualitative evaluation is done by ELMS spectra and the result is expressed in μg/mg toner.

This method may be used to detect the presence of aromatic acids and phenolic compounds, as being identified decomposition residues. Due to matrix effects and specific pigment interaction it is less usable to make quantitative predictions or measurements of migration or evaporation of residues. Tentative, a value of lower than 0.15 μg/mg toner may be estimated to be acceptable, based on the experiments described hereinbelow.

Chargebility-Developability Performance

A print test is carried out on a Xeikon 9600 print engine at a speed of 16 cm/s over 50.000 substrates with a cyan toner developer. The target optical density on the substrate is 1.4. The following sequence was subsequently printed:

A: 20.000 substrates were printed with a toner throughput of 50 mg/s.
B: 10.000 substrates were printed with a toner throughput of 5 mg/s
C: 5.000 substrates were printed with a toner throughput of 50 mg/s
D: 5.000 substrates were printed with a toner throughput of 300 mg/s Changes in the developer's chargeability and developability can result as a consequence in a change of amount of toner that is extracted and replenished per unit of time in a situation of continued printing. The toner throughput after long runs in regimes A, B, C or D typically affects the density at fixed development settings to a certain degree because of known effects of additive burial, speed of charging etc. For stable printing it is required to adapt development settings (field strength) or adjust toner density to the target level. Too low optical density requires an increase of the development field and a too high optical density requires a decrease in development field. In a reversal development process as used in the Xeikon 9600 the increase in the development field is induced by an increase of the exposure intensity and vice versa. The exposure intensity required to obtain the target optical density on the substrate was determined for each segment A, B, C and D.

A ranking of the chargeability-developability performance is as follows:

1=excellent performance: almost no difference in exposure intensity between A, B and D
3=good performance: small differences in exposure intensity between A, B and D
5=acceptable performance acceptable differences in exposure intensity between A, B and D
7=bad performance: too large differences in exposure intensity between A, B and D
10=unacceptable performance unacceptable differences in exposure intensity between A, B and D—a density of 1.4 could not be reach after printing B Toner Composition

TABLE 1A

| Ingredient | Description | Tm (° C.) | AV (mg KOH/g) |
|---|---|---|---|
| PM1 | polyester resin | 104 | 25 |
| PM2 | polyester resin | 93 | 24 |

Table 1A shows binder resin components, which are used to prepare toner compositions. PM1 and PM2 are both polyester resins, which are used as binder resins. The PM1 and PM2 have differencing melting temperatures (Tm; ° C.) and have similar acid values (AV; mg KOH/g) of about 24-25 mg KOH/g.

TABLE 1B

Figure 3:
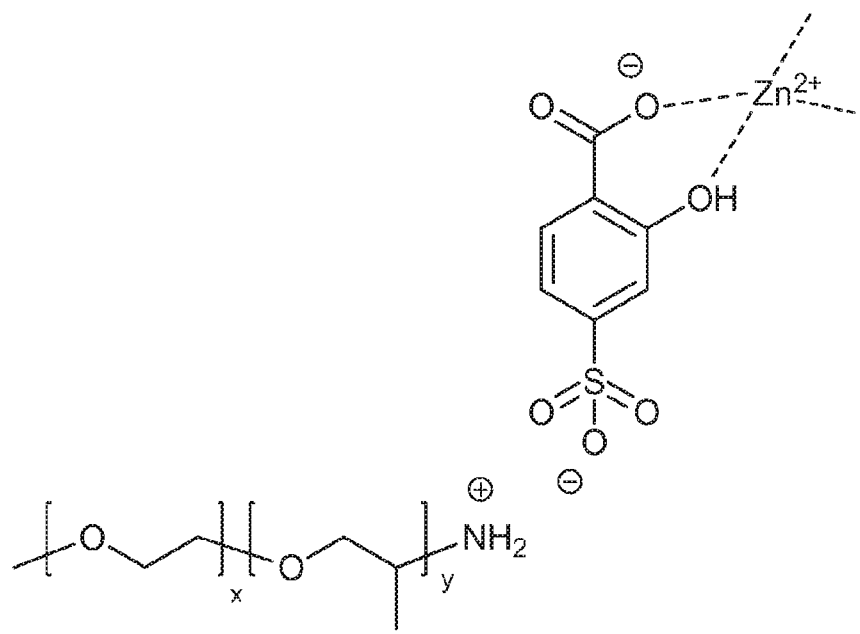
FIG. 3 illustrates schematically a molecular structure of a metal compound according to exemplary embodiments of the present invention.

| Ingredient | name | Mw (g/mol) | Polymer segment |
|---|---|---|---|
| CCA1 | Bontron E84 | 563 | — |
| CCA2 | FIG. 3 | 1500 | Jeffamine M-600 |
| CCA4 | FIG. 3 | 2300 | Jeffamine M-1000 |

TABLE 1B-continued

Figure 4:
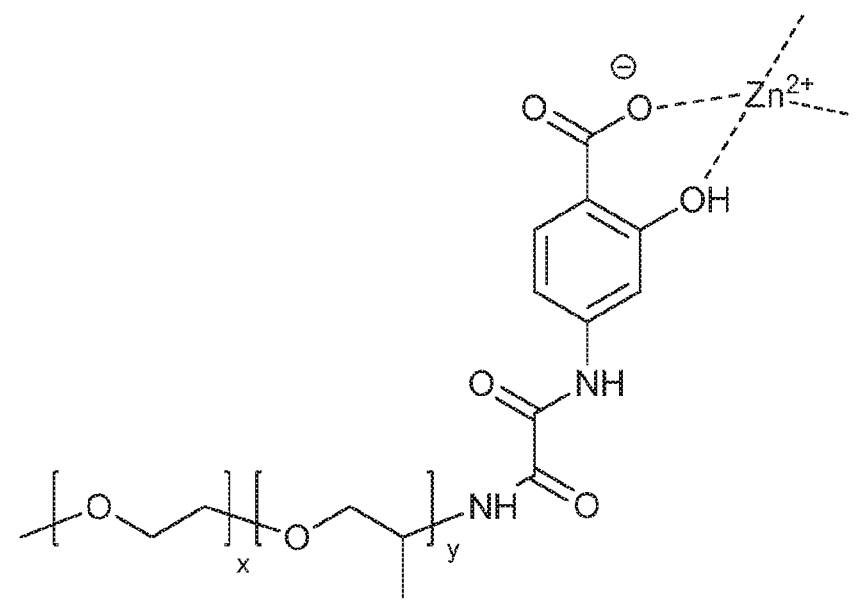
FIG. 4 illustrates schematically a molecular structure of a metal compound according to exemplary embodiments of the present invention.

| Ingredient | name | Mw (g/mol) | Polymer segment |
|---|---|---|---|
| CCA3 | FIG. 4 | 1500 | Jeffamine M-600 |
| CCA5 | Bontron E88 | 774 | |

Table 1B shows charge control agents components (CCA), which are used to prepare toner compositions. Bontron E84 and Bontron E88 are obtainable from Orient Chemical Industries Co. The molecular structure of the charge control agents CCA2 and CCA4 are schematically shown in FIG. 3, wherein the polymer segment is provided by a Jeffamine M-600 structure and a Jeffamine M-1000, respectively. In fact, the Jeffamine M-600 and the Jeffamine M-1000 comprises the polymer segment and a monoamine end group, which is used for forming a primary ammonium cation bonding group for bonding the polymer segment to the aromatic hydroxycarboxylic acid part. The material can be synthesized by warming up 120 g of Jeffamine M-600 (0.2 mol) to 110° C. and 50.84 g of 5-sulfosalicylic acid (0.2 mol, 1 eq.) is added to the hot polyetheramine. The resulting mixture is stirred for 30 min at 110° C., after which it was allowed to cool down to around 50° C. when methanol (200 ml) is added to the reaction mixture. To this solution is added 18.35 g of Zinc acetate (0.1 mol, 0.5 eq.) and the mixture is heated to reflux for 2 hours. After stirring under reflux for the appropriate time, the solution is evaporated under vacuum to yield the target salt.

The molecular structure of the charge control agents CCA3 is schematically shown in FIG. 4, wherein the polymer segment is provided by a Jeffamine M-600 structure. In fact, the Jeffamine M-600 comprises the polymer segment and a monoamine, which is used for forming an amide bonding group for covalently bonding the polymer segment to the aromatic hydroxycarboxylic acid part. The material can be synthesized by mixing together 11.96 g of Jeffamine M-600 (0.02 mol) and 2.92 g of diethyl oxalate (0.02 mol, 1 eq.) and heated to 135° C. for 1 hour. To the resulting product, 3.06 g of 4-aminosalicylic acid (0.02 mol, 1 eq.) is added and stirring at 135° C. is continued for another 3 hours. The reaction mixture is then allowed to cool down to around 50° C. when methanol (25 ml) is added. 1.83 g of zinc acetate is added to the resulting solution that is heated to reflux for 2 hours. After stirring under reflux for the appropriate time, the solution is evaporated under vacuum to yield the target product.

Also 5-aminosalicylic acid can be used instead of 4-aminosalicylic acid.

It is clear to the person skilled in the art that many other polymer segments may be bonded to the aromatic hydroxycarboxylic acid part instead of the poly(alkyleneoxide) segments.

The weight-average molar mass $M_w$ and the number-average molar mass $M_n$ of the polymer segment (or of the aromatic hydroxycarboxylic acid structure including the polymer segment) may be determined by Gel Permeation Chromatography (GPC) using polystyrene samples as standard.

Toner Preparation

The toners T1-T9 were prepared by melt blending for 30 minutes in a laboratory kneader at 110° C. the ingredients, including the specific metal compound CCA1-CCA5, as indicated in Table 2, together with 3% by weight of a phtalocyanine blue pigment for the cyan toner, 4% by weight of a PR57:1 for a magenta toner, 4% by weight of a PY185 for a yellow toner and 5% of carbon black for the black toner, as mentioned in table 2. The indicated mass % of the charge control agents CCA is the mass % based on the weight of the toner composition. After cooling, the solidified mass was pulverized and milled using an Alpine Fliessbett-gegenstrahlmuhle 100AFG (trade name) and further classified using a multiplex zig-zag classifier type 100MZR (trade name) to obtain a toner with a Dv50 between 7 and 9 μm.

As used herein, Particle Size Distribution D50 is also known as the median diameter or the medium value of the particle size distribution, it is the value of the particle diameter at 50% in the cumulative distribution. It is one of an important parameter characterizing particle size. For example, if D50=5.8 um, then 50% of the particles in the sample are larger than 5.8 um, and 50% smaller than 5.8 um. D50 is usually used to represent the particle size of group of particles. Dv50 is also known as volume median or volume average particle size, it physically represents that each volume of particles greater or smaller than such value takes account of 50% of the total particles volume.

In order to improve the flowability of the toner, the particles were mixed with 0.5% by weight of hydrophobic colloidal silica from Degussa.

Table 2—Toner Composition

TABLE 2 toner composition

| Toner | Polymer 1 | Polymer 2 | Conc PM1 [mass % of binders] | Conc PM2 [mass % of binders] | CCA | Conc CCA [mass %] |
|---|---|---|---|---|---|---|
| T1 | PM1 | PM2 | 50 | 50 | CCA1 | 1 |
| T2 | PM1 | PM2 | 50 | 50 | CCA1 | 0.5 |
| T3 | PM1 | PM2 | 50 | 50 | CCA1 | 0.2 |
| T4 | PM1 | PM2 | 50 | 50 | CCA2 | 1 |
| T5 | PM1 | PM2 | 50 | 50 | CCA3 | 2 |
| T6 | PM1 | PM2 | 50 | 50 | CCA2 | 2 |
| T7 | PM1 | PM2 | 50 | 50 | CCA2 | 4 |
| T8 | PM1 | PM2 | 50 | 50 | CCA4 | 4 |
| T9 | PM1 | PM2 | 50 | 50 | CCA5 | 1 |

Developers From toners T1 to T9 developers were prepared by mixing said toner particles together with coated silicone MnMgSr ferrite carrier with a Dv50 of 45 μm in a ratio of 7/100.

Images were printed on substrates using a Xeikon 9600 duplex engine at a speed of 16 cm/s Results

TABLE 3 toner behaviour

| Toner | CCA | Conc CCA [mass %] | Deposition in engine [/] | Chargebility [/] |
|---|---|---|---|---|
| T1 | CCA1 | 1 | 3 | 1 |
| T2 | CCA1 | 0.5 | 2 | 7 |
| T3 | CCA1 | 0.2 | 1 | 10 |
| T4 | CCA2 | 1 | 1 | 5 |
| T5 | CCA3 | 2 | 1 | 3 |
| T6 | CCA2 | 2 | 1 | 3 |
| T7 | CCA2 | 4 | 2 | 1 |
| T8 | CCA4 | 4 | 1 | 3 |
| T9 | CCA5 | 1 | 3 | 1 |

From the data shown in table 3, it can be learned that by reducing the concentration of CCA1 in the toner (see T1 to T3) the deposition or formation of tert-butylsalicylic acid and/or di-tert-butyl phenol can be reduced but the chargeability of the toner is reduced to unacceptable levels. Sample T9 shows that by changing the metal ion, from Zinc of the Bontron E84 to Aluminum of the Bontron E88, the problem can not be solved.

Furthermore, it can be learned that by bonding the charge control agent to a polymer segment the formation of an easily migrating aromatic hydroxycarboxylic acid structure residue, such as a tert-butylphenol and tert-butylsalicylic acid, is reduced or eliminated, and thus also the deposition of such a aromatic hydroxycarboxylic acid structure residue in the engine can be strongly reduced while not substantially affecting the charging behavior of the toner, (see T4 to T8).

By the fact that the molecular weight Mw of the CCA of the exemplary embodiments of the current invention is higher, more CCA is needed to have the a similar charging behavior. However the higher CCA concentration has only a limited effect on the tert-butylsalicylic acid and/or tert-butyl phenol release or deposition in the engine (see T4, T6, T7)

Whilst the principles of the invention have been set out above in connection with specific embodiments, it is to be understood that this description is merely made by way of example and not as a limitation of the scope of protection which is determined by the appended claims.

The invention claimed is:

1. A metal compound comprising a metal (M) and first and second aromatic hydroxycarboxylic acid structures (S1, S2), each aromatic hydroxycarboxylic acid structure (S1, S2) having an aromatic moiety (A1, A2) having a hydroxyl substituent and a carboxylic acid substituent, which cooperatively bond the aromatic moiety (A1, A2) to the metal (M) via at least one of ionic bond, covalent bond and coordinate bond, wherein each of said first and second aromatic hydroxycarboxylic acid structures (S1, S2) is bonded to a polymer segment (P) via a bonding group (B) that is configured for bonding the polymer segment (P) to the respective aromatic moiety (A1, A2);
    wherein said bonding group (B) comprises an amide and/or a carboxylic acid ester;
    wherein the polymer segment (P) is defined as a sequence of monomer repeating units and has has a molecular weight of at least 500 g/mol, and
    wherein the weight average molecular weight Mw of the aromatic hydroxycarboxylic acid structure including the polymer segment is at least 500 g/mol.

2. The metal compound according to claim 1, wherein the weight average molecular weight Mw of the aromatic hydroxycarboxylic acid structure including the polymer segment is at least 1000 g/mol.

3. The metal compound according to claim 1, wherein the metal is selected from a zirconium atom, a calcium atom, an aluminum atom, a chromium atom, an iron, a boron atom and a zinc atom.

4. The metal compound according to claim 1, wherein the aromatic moiety (A1, A2) having the hydroxyl substituent and the carboxylic acid substituent is selected from a group consisting of a salicylic acid, a salicylic acid having one or more additional substituents, a hydroxynaphtoic acid and a hydroxynaphtoic acid having one or more additional substituents.

5. The metal compound according to claim 1, wherein the polymer segment (P) is defined as a sequence of monomer repeating units having a molecular weight of at least 500 g/mol, and comprises at least one of an alkyleneoxide group, an olefin group, an ester group, an acrylic group, a vinylether group, a vinylester group, and a vinylamide group.

6. The metal compound according to claim 1, wherein the polymer segment (P) is a copolymer segment with a molecular weight of at least 500 g/mol; said copolymer comprising at least one of an ethylene oxide repeating unit, a propylene oxide repeating unit and a butylene oxide repeating unit.

7. The metal compound according to claim 1, wherein the weight average molecular weight Mw of the polymer segment (P) is defined as a sequence of monomer repeating units in the range of 1000 g/mol-2500 g/mol.

8. The metal compound according to claim 1, wherein each aromatic hydroxycarboxylic acid structure (S1, S2) comprises a polymer segment (P1, P2), wherein a first polymer segment (P1) of a first aromatic hydroxycarboxylic acid structure (S1) and a second polymer segment (P2) of a second aromatic hydroxycarboxylic acid structure (S2) are equal to one another or are different with respect to one another.

9. The metal compound according to claim 1, wherein the polymer segment (P) is bonded to both the first and second aromatic hydroxycarboxylic acid structures (S1, S2), thereby connecting the first aromatic hydroxycarboxylic acid structure (S1) to the second aromatic hydroxycarboxylic acid structure (S2) such that both aromatic hydroxycarboxylic acid structures (S1, S2) need to be released from the metal (M) before a loose aromatic hydroxycarboxylic acid structure can be formed.

10. The metal compound according to claim 1, wherein the bonding group is a substituent of the aromatic moiety configured for forming an ionic bond to the polymer segment.

11. The metal compound according to claim 1, wherein the weight average molecular weight Mw of the aromatic hydroxycarboxylic acid structure including the polymer segment is at least 500 g/mol and at most 3500 g/mol.

12. The metal compound according to claim 1, wherein the bonding group (B) comprises a diamide.

13. A metal compound comprising a metal (M) and first and second aromatic hydroxycarboxylic acid structures (S1, S2) connected via a bridging polymer segment (Pb), wherein both aromatic hydroxycarboxylic acid structures (S1, S2) have an aromatic moiety (A1, A2) having a hydroxyl substituent and a carboxylic acid substituent, wherein the hydroxyl substituents and carboxylic acid substituents cooperatively bond the respective aromatic moiety (A1, A2) of both the first and second aromatic hydroxycarboxylic acid structures (S1, S2) to the metal (M) via at least one of an ionic bond, a covalent bond and a coordinate bond, wherein said first and second aromatic hydroxycarboxylic acid structures (S1, S2) are both bonded to the bridging polymer segment (Pb) which connects the first and second aromatic hydroxycarboxylic acid structures (S1, S2) such that both aromatic hydroxycarboxylic acid structures (S1, S2) need to be released from the metal (M) before a loose aromatic hydroxycarboxylic acid structure can be formed, wherein the weight average molecular weight Mw of the aromatic hydroxycarboxylic acid structure including the bridging polymer segment (Pb) is at least 500 g/mol.

14. The metal compound according to claim 13, wherein at least two bonding groups (B) are included, wherein a first bonding group (B) connects the bridging polymer segment (Pb) to the first aromatic hydroxycarboxylic acid structure (S1), and a second bonding group (B2) connects the bridging polymer segment (Pb) to the second one of the two aromatic hydroxycarboxylic acid structure (S2).

15. The metal compound according to claim 13, wherein the bridging polymer (Pb) has an average molecular weight of at least at least 500 g/mol.

16. A metal compound comprising a metal (M) and at least two aromatic hydroxycarboxylic acid structures (S1, S2), each aromatic hydroxycarboxylic acid structure (S1, S2) having an aromatic moiety (A1, A2) having a hydroxyl substituent and a carboxylic acid substituent, which cooperatively bond the aromatic moiety (A1, A2) to the metal (M) via at least one of ionic bond, covalent bond and coordinate bond, wherein each aromatic hydroxycarboxylic acid structure (S1, S2) is bonded to a polymer segment (P) defined as a sequence of one or more types of monomer repeating units; said polymer segment (P) being a copolymer and having an average molecular weight of at least 500 g/mol; wherein the weight average molecular weight Mw of the aromatic hydroxycarboxylic acid structure including the polymer segment is at least 500 g/mol.

17. The metal compound according to claim 16, wherein the copolymer segment is represented by

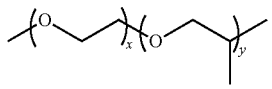

wherein X is an integer from 1 to 3; Y is an integer from 9 to 19; and has an average molecular weight of at least at least 500 g/mol.

18. The metal compound according to claim 16, wherein the copolymer has a molecular weight of at least 1000 g/mol.

\* \* \* \* \*